United States Patent
Weinberg

(10) Patent No.: US 11,640,585 B2
(45) Date of Patent: May 2, 2023

(54) METHOD FOR CUSTOMIZABLE PRIORITY WAIT LIST NOTIFICATION FOR APPOINTMENTS

(71) Applicant: Andrew Mark Weinberg, Scottsdale, AZ (US)

(72) Inventor: Andrew Mark Weinberg, Scottsdale, AZ (US)

(73) Assignee: Andrew Mark Weinberg, Scottsdale, AZ (US)

( * ) Notice: Subject to any disclaimer, the term of this patent is extended or adjusted under 35 U.S.C. 154(b) by 177 days.

(21) Appl. No.: 16/889,499

(22) Filed: Jun. 1, 2020

(65) Prior Publication Data

US 2021/0216971 A1 Jul. 15, 2021

Related U.S. Application Data

(60) Provisional application No. 62/959,696, filed on Jan. 10, 2020.

(51) Int. Cl.
*G16H 10/60* (2018.01)
*G06Q 10/1093* (2023.01)
*H04W 4/12* (2009.01)
*G06Q 10/02* (2012.01)
*G16H 40/20* (2018.01)

(52) U.S. Cl.
CPC ......... *G06Q 10/1095* (2013.01); *G06Q 10/02* (2013.01); *G16H 10/60* (2018.01); *G16H 40/20* (2018.01); *H04W 4/12* (2013.01)

(58) Field of Classification Search
CPC .... G06Q 10/1095; G06Q 10/02; G16H 40/20; G16H 10/60; H04W 4/12
See application file for complete search history.

(56) References Cited

U.S. PATENT DOCUMENTS

| 7,689,441 | B1 | 3/2010 | Craft | |
|---|---|---|---|---|
| 7,991,637 | B1 * | 8/2011 | Guiheneuf | ......... G06Q 10/1095 705/7.18 |
| 2006/0230115 | A1 * | 10/2006 | Brooke | ................ G06Q 10/109 709/206 |
| 2007/0282656 | A1 | 12/2007 | Battcher et al. | |

(Continued)

OTHER PUBLICATIONS

OpenTable, https://www.opentable.com/.
MyStandby, https://www.mystandby.com/.

*Primary Examiner* — Mark Holcomb

(57) ABSTRACT

A method developed for providing patients and health care providers with an efficient and customizable way to manage abrupt cancellations. In order to accomplish that, the method of the present invention successfully matches desired time slots from an appointment request created by a patient account with recently available time slots posted by a health care provider account. The method then generates a queue comprised of patient account appointment requests where the order of the patient accounts appointment requests depends on the preferred criteria set by the health care provider accounts in the health industry. Further, the method of the present invention enables the health care provider account to choose a standard queue generated, where the patient accounts are placed in the queue in chronological order of the wish list entry or to use one or more different algorithms alone or in combination to generate weighted composite queues.

3 Claims, 7 Drawing Sheets

(56) References Cited

U.S. PATENT DOCUMENTS

| | | | |
|---|---|---|---|
| 2010/0070295 A1* | 3/2010 | Kharraz Tavakol | G16H 40/20 |
| | | | 705/2 |
| 2014/0257879 A1 | 9/2014 | Sink et al. | |
| 2015/0220887 A1 | 8/2015 | Peres et al. | |
| 2015/0286992 A1 | 10/2015 | Dewane | |
| 2017/0124521 A1 | 5/2017 | Lee et al. | |
| 2017/0337520 A1* | 11/2017 | Spencer | G06Q 10/1095 |
| 2020/0143938 A1* | 5/2020 | Kakhki | G06Q 10/109 |

* cited by examiner

| Parameter | Patient A | Weighted | Patient B | Weighted | Weighting Factor |
|---|---|---|---|---|---|
| Date of appointment request creation | 1 | 0 | 2 | 0 | 0 |
| Symptom | 1 | .5 | 2 | 1 | 0.5 |
| Medical History Risk Score | 2 | 2 | 3 | 3 | 1 |
| Insurance Plan | 3 | 3.75 | 2 | 2.5 | 1.25 |
| Total appointment request score | | 6.25 | | 6.5 | |

FIG. 6

METHOD FOR CUSTOMIZABLE PRIORITY WAIT LIST NOTIFICATION FOR APPOINTMENTS

The current application claims a priority to the U.S. Provisional Patent application Ser. No. 62/959,696 filed on Jan. 10, 2020.

FIELD OF THE INVENTION

The present invention relates generally to a method for managing cancellations for patient appointments in the health care industry. More specifically, the present invention comprises a method which uses weighted algorithms to create a queue for patients requesting a particular date and time for an appointment, rather than an automatic nonadjustable waitlist.

BACKGROUND OF THE INVENTION

In present times, if a patient is in need of any non-emergency medical services, they schedule an appointment to be seen by their health care provide of choice. Unfortunately, patients are limited by the availability of the provider, which usually leads to patients requesting time off-work and having to accommodate their schedule to meet the available less desired appointment times of the provider. Furthermore, when a patient cancels abruptly, the appointment is hardly ever filled in time by current methods. Patients looking to be notified of a cancellation have no means other than to keep looking at the doctor's appointment calendar for openings and the doctor office has no way of retaining which appointment times and days a specific patient can fill if a cancellation occurs. This inefficiency usually leads to a financial loss or double-booking other time slots to compensate. Further, when providers double book times slots and all the patients show up, this results in provider delays, lower patient satisfaction, and higher levels of stress for the provider. Medical imaging centers and elective surgery centers also suffer cancellations and can benefit from a system that automatically fills these cancelled spots. In order to solve this issue some providers keep a manual list of patients who wish an earlier slot, but the providers do not know a specific time or date the patient prefers. Therefore, even if a time slot is suddenly available, this does not necessarily mean that the patients on the waitlist will be available for the new time slot. Many time-consuming phone calls have to be made by office staff to find someone who can fill the slot. Thus, it is important to provide patients with a more efficient way to find out when a time slot suddenly becomes available, other than constantly calling or logging into the provider's online portal. Recently providers have implemented scheduling manager platforms that improve upon this aspect, but the platforms lack sufficient versatility and technology in order to successfully resolve this issue.

It is an objective of the method of the present invention to provide a solution to the above-mentioned problems by empowering patients and health care providers with an efficient and customizable method that can manage abrupt cancellations. In other words, the present invention is primarily developed to provide a customized wait list that can effectively improve patient care by providing better patient compliance and needed care in a timely manner, thereby improving patient satisfaction. In order to accomplish that, the present invention successfully matches desired time slots from a wish list created by a patient account with recently available time slots posted by a health care provider account. The present invention then generates a queue comprised of patient account wish lists where the order of the patient accounts wish lists depends on the preferred criteria set by the health care provider accounts in the health industry. Further, the health care provider account can choose to have a standard queue generated, where the patient accounts are placed in the queue in chronological order of the wish list entry. The health care provider account can also choose to use one or more different algorithms alone or in combination in order to generate weighted composite queues based on one or more different factors. Thus, the method of the present invention enables office staff of the provider's office to save time by avoiding having to use manual wait lists and calling patients. The method of the present invention improves revenue of the healthcare provider by keeping the schedules full despite last minute cancellations and avoiding the need to double book patients.

SUMMARY OF THE INVENTION

The present invention is a method primarily developed for providing patients and health care providers with an efficient and customizable way to manage abrupt cancellations. In order to accomplish that, the present invention successfully matches desired time slots from a wish list created by a patient account with recently or subsequently available time slots posted by a health care provider account. The present invention then generates a queue comprised of patient account wish lists where the order of the patient accounts wish lists depends on the preferred criteria set by the health care provider accounts in the health industry. Further, the health care provider account can choose to have a standard queue generated, where the patient accounts are placed in the queue in chronological order of the wish list entry, or choose to use one or more different algorithms alone or in combination provided by the present invention which generate weighted composite queues based on one or more different factors. Thus, the method of the present invention further enables the provider's office to save time by avoiding manual wait lists and improves revenue by keeping the schedules full and avoiding double booking of patients due to abrupt cancellations.

BRIEF DESCRIPTION OF THE DRAWINGS

FIG. 6 is a table illustrating an example for using a weighted score according to one embodiment of the method of the present invention.

DETAIL DESCRIPTIONS OF THE INVENTION

All illustrations of the drawings are for the purpose of describing selected versions of the present invention and are not intended to limit the scope of the present invention.

The present invention is a method primarily developed for providing patients and health care providers with an efficient and customizable way to manage abrupt cancellations. In order to accomplish that, the present invention successfully matches desired time slots from a wish list created by a patient account with recently available time slots posted by a health care provider account. The present invention then generates a queue comprised of patient account wish lists where the order of the patient accounts wish lists depends on the preferred criteria set by the health care provider accounts in the health industry. Further, the health care provider account can choose to have a standard queue generated, where the patient accounts are placed in the queue in chronological order of the wish list entry. Furthermore, the health care provider account can also choose to use one or more different algorithms alone or in combination, in order to generate weighted composite queues based on one or more different factors. Thus, the method of the present invention enables the provider's office staff to save time by avoiding manual wait lists and improve revenue by keeping the schedules full and avoiding double booking of patients due to abrupt cancellations. The same value proposition is true for outpatient hospital, free standing elective surgery or procedure centers, imaging centers, and outpatient labs.

Figure 1:
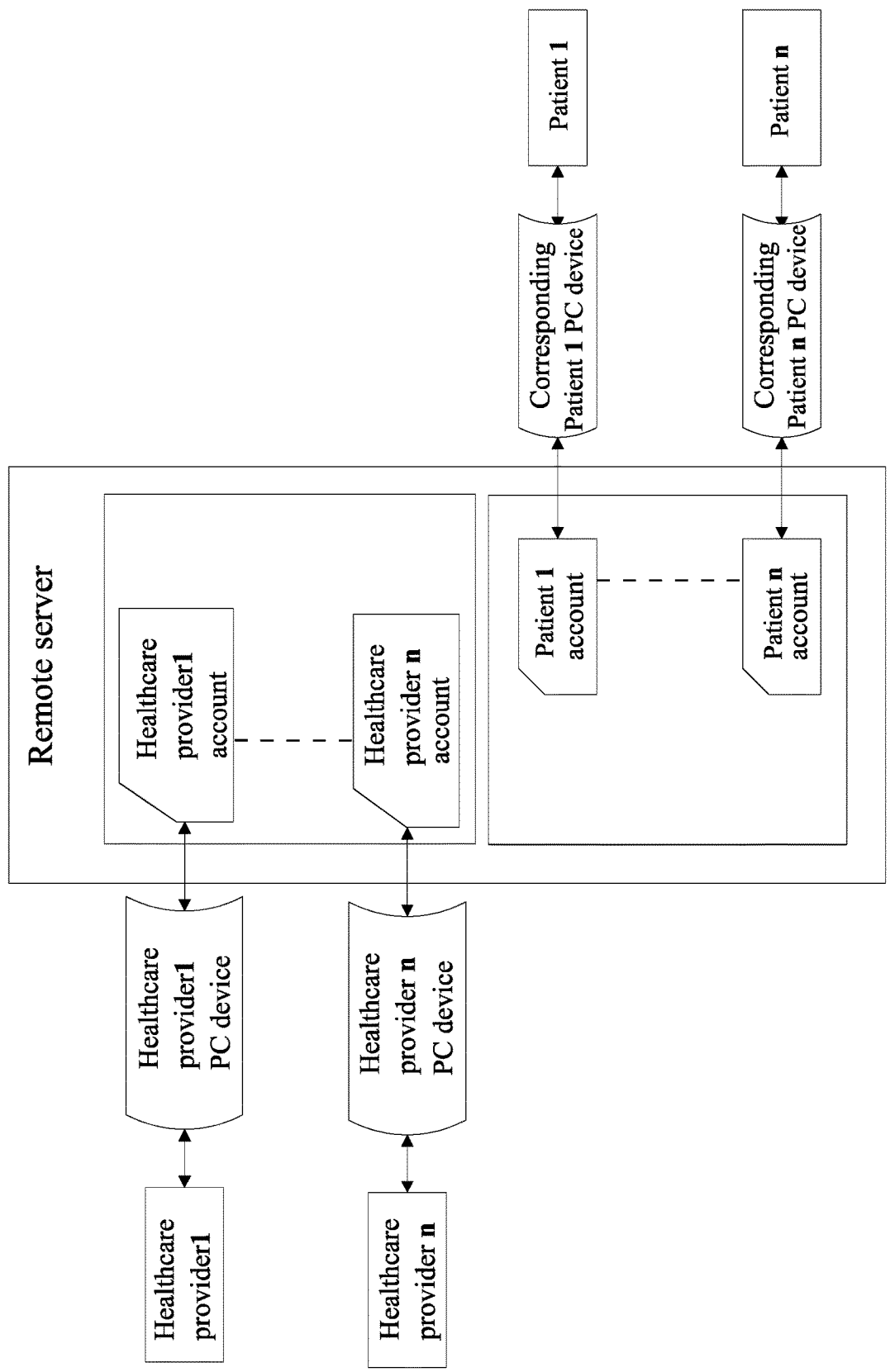
FIG. 1 is a block diagram illustrating a system overview of the present invention.

The following description is in reference to FIG. 1 through FIG. 7. As can be seen in FIG. 1, the system used to execute the method of the present invention allows the present invention to function as a communication tool between multiple users. To accomplish this, the method of the present invention associates each of the plurality of users with a unique user account from a plurality of user accounts that is managed by a remote server. The plurality of user accounts is divided into a plurality of healthcare provider accounts, (healthcare provider 1 through healthcare provider n) and a plurality of patient accounts (patient 1 through patient n). As seen in FIG. 1, the system comprises at least one healthcare provider account managed by at least one remote server, wherein the healthcare provider account is associated with a corresponding provider personal computing (PC) device, and wherein the healthcare provider account includes a plurality of appointment timeslots (Step A). Available time slots of a healthcare provider account are referred to as appointment timeslots. Similarly, the system used to execute the method of the present invention comprises a plurality of patient accounts managed by the remote server, wherein each patient account is associated with a corresponding patient PC device (Step B). In other words, each of the plurality of user accounts is associated with a corresponding user personal computing (PC) device. The corresponding user PC devices used to interact with the present invention can be, but is not limited to, a smartphone, a laptop, a desktop, or a tablet PC, or any apparatus with an operating system compatible to access the cloud-based software platform. The remote server is used to facilitate communication between the plurality of user accounts. Moreover, the remote server is used to execute a number of internal processes for the present invention and is used to store message data. Additionally, the system used to execute the method of the present invention comprises a cloud-based HIPAA complaint software platform capable of storing data from the wish list created by a patient account. For example, the cloud-based remote server(s) stores data regarding each corresponding PC device, patient's personal information, health records, insurance information and the desired time slots. The corresponding patient PC device allows the patient account to perform computer functions such as generating a wish list which contains ranges of dates and times that are most convenient for the patient and are sooner than their existing appointment. The corresponding patient PC device allows the patient account to access the platform and generate the required information that will be relayed to the cloud-based remote server(s) and to other corresponding healthcare provider PC devices. Preferably, the software platform that runs the method of the present invention is a stand alone system and a web app or traditional app that overlies a medical entity scheduling module, but the software program can be modified to work as an app. The software program may be directly integrated into an existing scheduling module, may be used as a plug in on top of an existing scheduling module, or be connected by an HL7 API interface.

Figure 2:
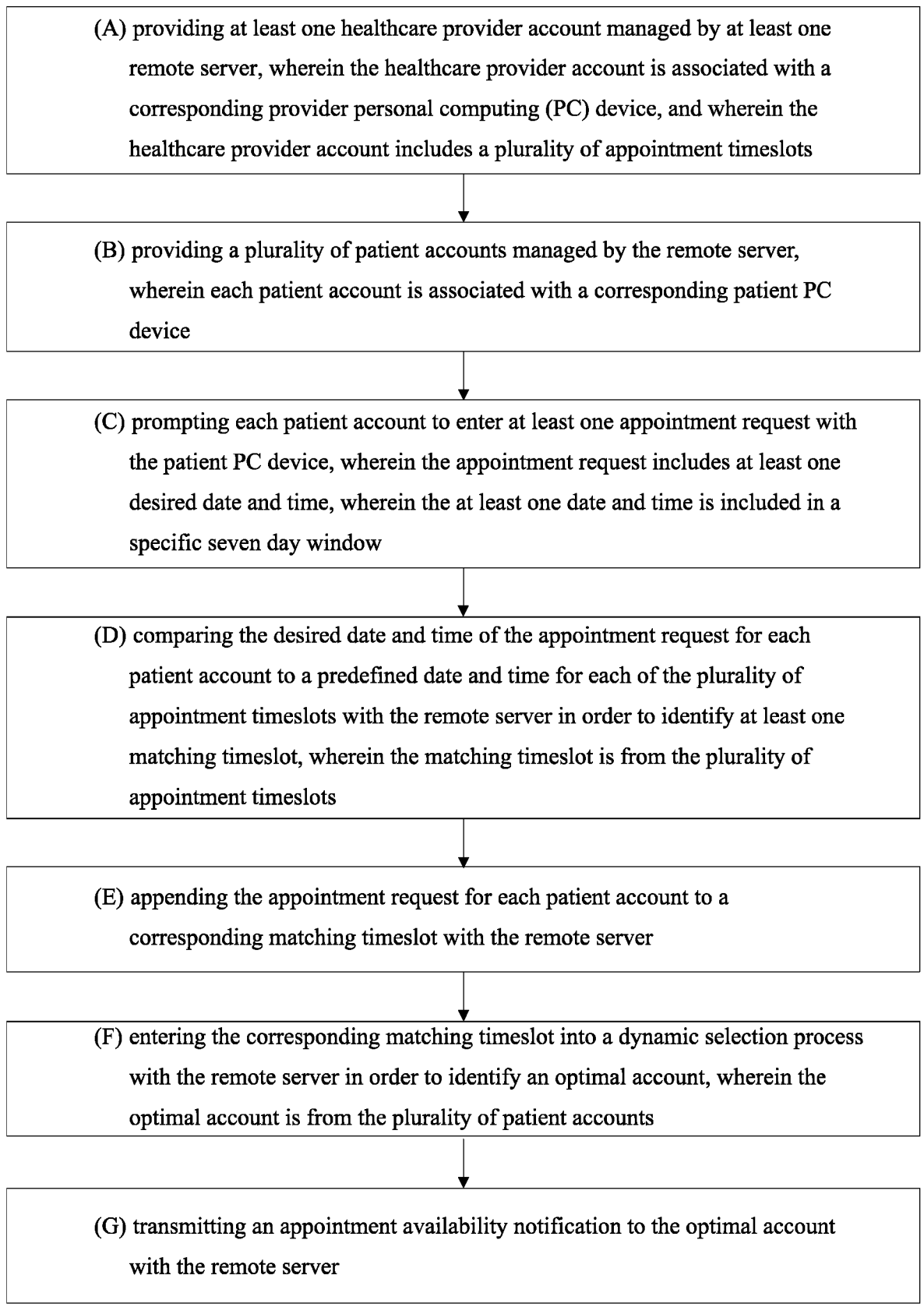
FIG. 2 is a flowchart describing an overall process followed by the method of the present invention.

As can be seen in FIG. 2, the overall method of the present invention accomplishes the above described functionalities by first prompting each patient account to enter at least one appointment request (wish list) with the patient PC device, wherein the appointment request includes at least one desired date and time, and wherein the at least one date and time is included in a specific seven day window (Step C). For example, patient X can enter Monday, between 10-11 AM as his desired date and time in his appointment request. Further, the method of the present invention prompts the patient account to enter at least one patient datum into the appointment request with the patient PC device. According to the preferred embodiment of the method of the present invention, the at least one patient datum is selected from a group of parameters, examples of which include, but are not limited to, at least one desired date and time, at least one specific seven-day window, at least one provider account, provider group, provider specialty, network status, and distance of a provider practice from a patient-selected location. However, any other patient data that is known to one of ordinary skill in the art may be entered, as part of the appointment request. each wish list the patient can select the provider, provider group, or specialty to search for against posted availabilities. Further, a patient may select a patient data to match against a network status (in network, out of network or both). For example, Z is a young mom with several kids. She needs to get her GYN appointment within a 2 hour interval on a Tuesday or Thursday this month due to child care constraints. In her appointment request, she puts in a time range on Tuesday and Thursday. The system executing the present method copies the range each week until her current appointment in 6 weeks. Further, Z can navigate the access to the system from mobile device or desktop computer. Furthermore, the method of the present invention can provide matches for various provider accounts, examples of which include, but are not limited to a medical practice, a surgical procedure center, imaging center, urgent care center, endoscopy center, laboratory center etc.

Figure 3:
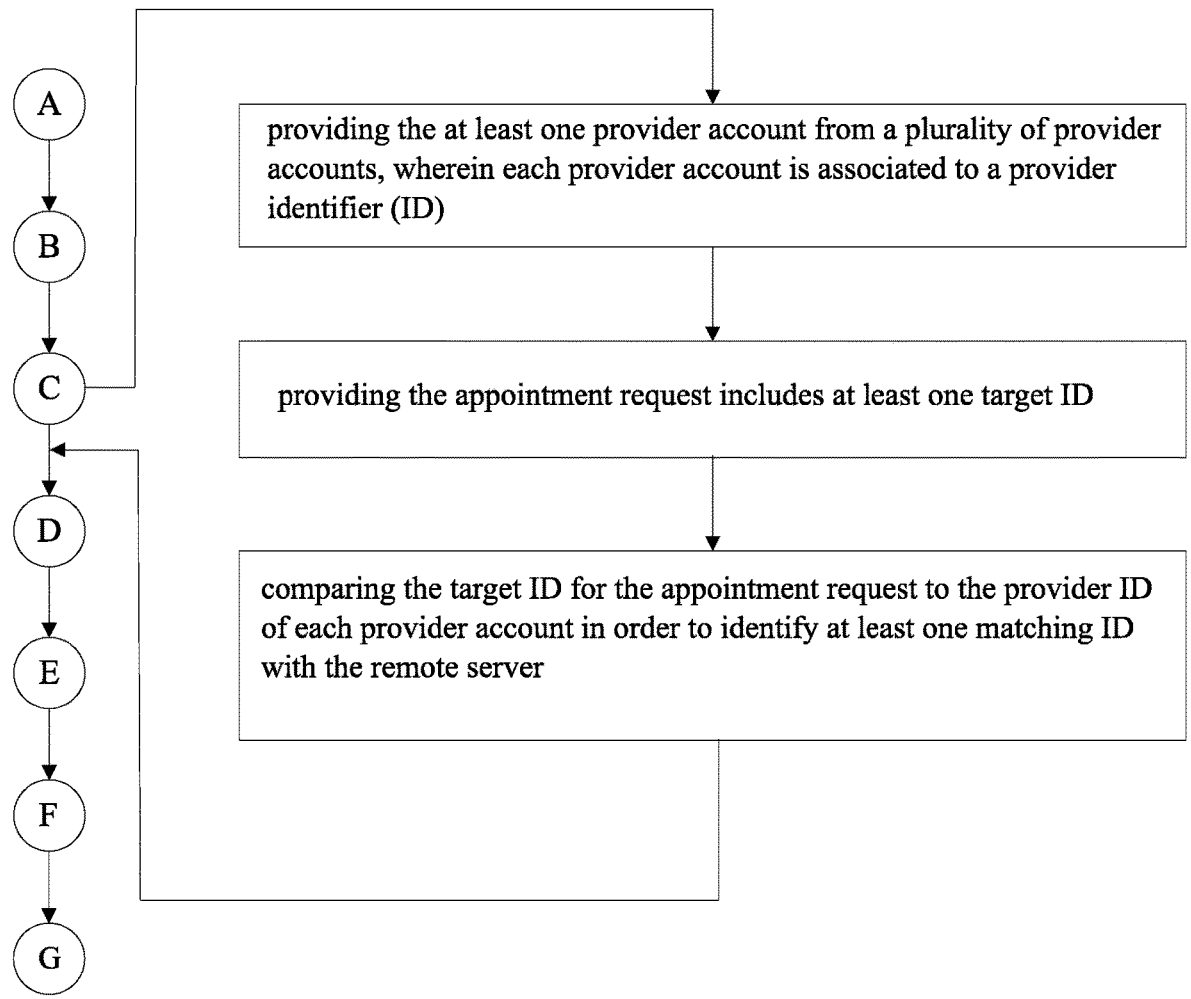
FIG. 3 is a flowchart describing a sub-process for choosing the correct provider account from a plurality of provider accounts.

As can be seen in FIG. 3, a sub-process of the method of the present invention enables the ability for a patient to choose the correct provider account from a plurality of provider accounts. According to the sub-process the method provides at least one provider account from a plurality of provider accounts, wherein each provider account is associated to a provider identifier (ID). The sub-process continues by providing at least one target ID, which is included in the appointment request entered by the patient account. Further, the target ID from the appointment request is compared to the provider ID of each provider account in order to identify at least one matching ID with the remote server. For example, a patient account could specify cardiology within 25 miles from a zip code or address for hypertension diagnosis to be on multiple healthcare provider accounts at the same time. This greatly increases the chances of a preliminary match occurring.

Figure 4:
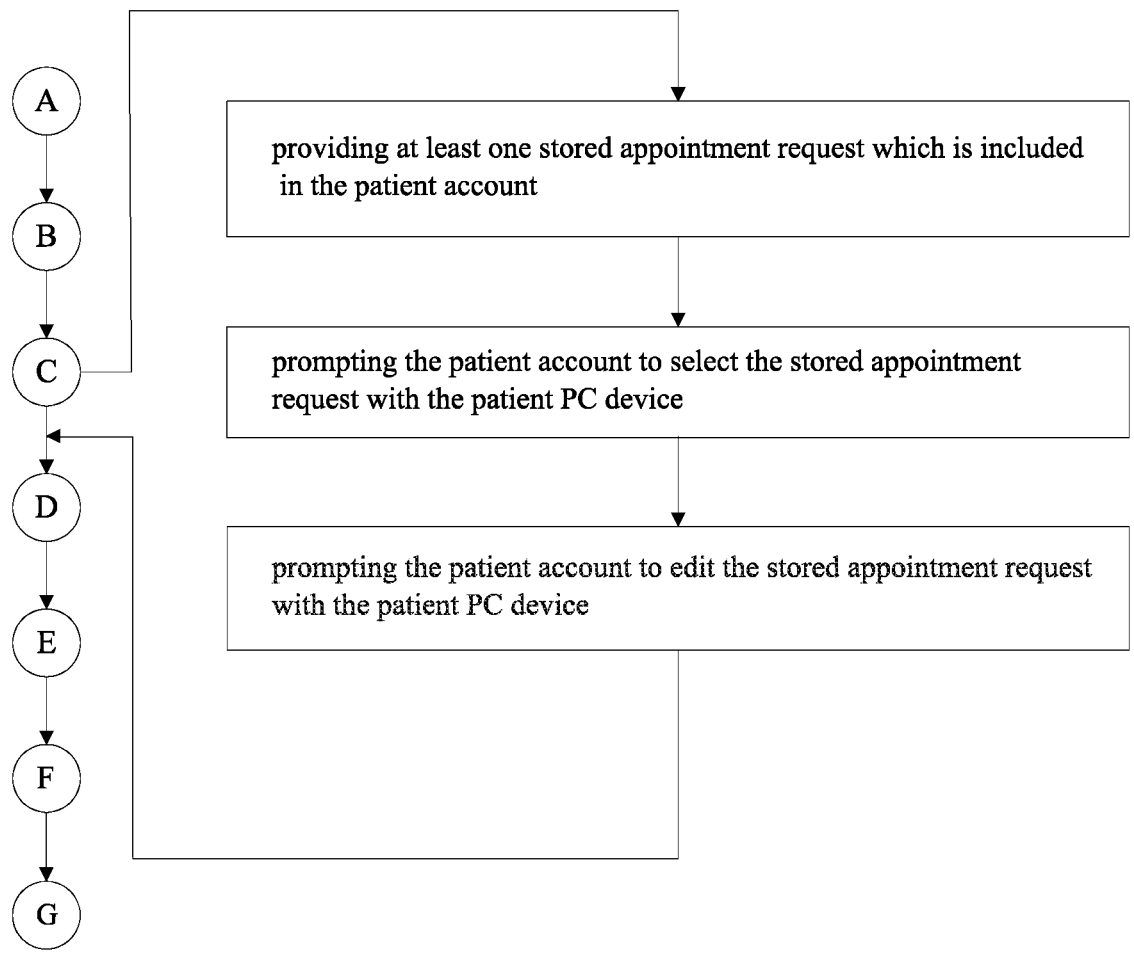
FIG. 4 is a flowchart describing a sub-process for selecting and editing a stored appointment request for a patient.

As can be seen in FIG. 4, a sub-process of the method of the present invention enables a patient to copy and edit a stored appointment request of that patient. Accordingly, the sub-process begins by providing the patient at least one stored appointment request which is included in the patient account. Further, the patient account is prompted to copy the stored appointment request with the patient PC device. The sub-process continues by providing the option to edit the stored appointment request with the patient PC device. Furthermore, the method of the preferred embodiment of the present invention continues by prompting the patient account to select a specific time frame with the patient PC device, wherein the stored appointment request is periodically transmitted to the remote server for comparing with provider ID until an end date of the specified time frame or until an appointment availability notification is received. In other words, a weekly schedule can be made to repeat so the same pattern does not have to be entered on a calendar week after week. A prior stored appointment pattern request, a "wish list" can be copied for future use for the same or a different provider appointment request without having to enter the pattern again. For example, a stored appointment request of patient X includes Monday 10-11 AM as a preferred slot. While entering a new appointment request, patient X can edit the preferred slot of stored appointment request to Tuesday 4-5 PM. The rest of the patient data int the stored appointment request may be edited or kept as is, depending on the patient requirements. As a second example a stored appointment request comprising a dental appointment may be used or modified for a primary care appointment later. Further, according to the preferred embodiment of the method of the present invention, the stored appointment request may be periodically transmitted (sent every week) to the remote server for a specific time frame, such as for 2 months, or until an appointment availability notification is received from the provider Y.

As can be seen in FIG. 2, the overall method of the present invention continues by comparing the desired date and time of the appointment request for each patient account to a predefined date and time for each of the plurality of appointment timeslots with the remote server in order to identify at least one matching timeslot. The matching timeslot is from the plurality of appointment timeslots (Step D). In other words, the cloud-based remote server(s) compares the plurality of available timeslots (from Step A) associated with each of the plurality of healthcare provider accounts, to the desired date and time of each appointment request to find the matching timeslot.

As can be seen in FIG. 2, the overall method of the present invention continues by appending the appointment request for each patient account to a corresponding matching timeslot with the remote server (Step E). In other words, after finding the matching timeslot for a patient account (through step D), the appointment request for each patient account that falls under the matching timeslot is appended or tagged as the corresponding matching timeslot.

In case of multiple patient accounts having requested the same timeslot, the cloud-based remote server(s) will generate a queue of patient accounts that best correspond to the matching timeslot. In order to accomplish that, the overall method of the present invention proceeds by entering the corresponding matching timeslot into a dynamic selection process with the remote server. This enables to identify an optimal account, wherein the optimal account is from the plurality of patient accounts (Step F).

Figure 5:
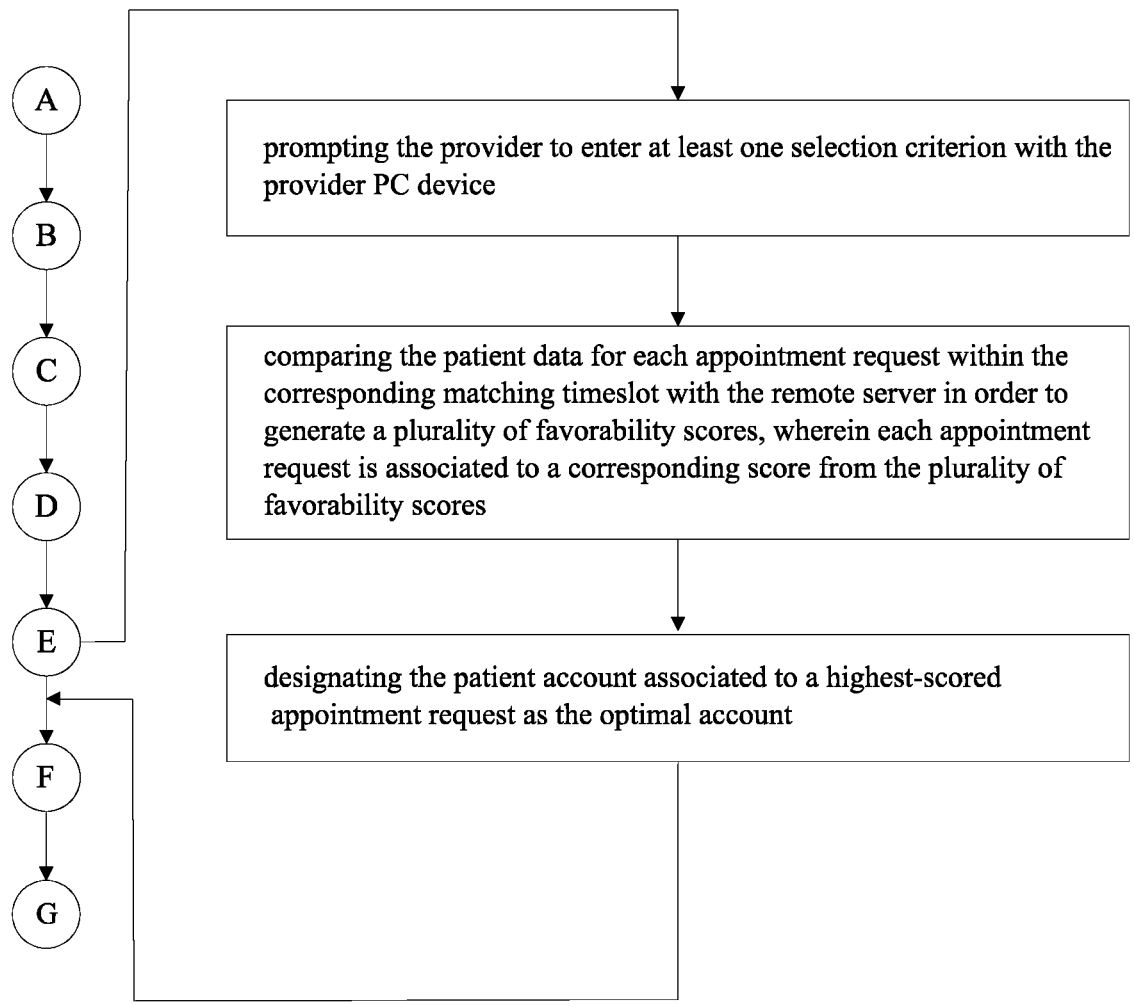
FIG. 5 is a flowchart describing a sub-process for selecting an optimal patient account through a dynamic selection process.

As can be seen in FIG. 5, the sub-process of the method of the present invention for selecting an optimal patient account through the dynamic selection process may be described as follows. According to the method of the present invention, wherein the appointment request includes patient data, the sub-process may be executed based on the patient data entered by the plurality of patient accounts. The sub-process starts by prompting the provider to enter at least one selection criterion with the provider PC device. The cloud-based remote server(s) provides the health care provider accounts with a posting availability option, thereby enabling the healthcare provider to select a particular selection criterion. According to the preferred method of the present invention, the selection criteria is at least one datapoint selected from the group consisting of, insurance plan type, chief complaint for the visit, symptoms, patient diagnosis, prior health history, prior patient health costs, severity of illness, and concierge status. However, any other selection criterion that is known to one of ordinary skill in the art may be entered by the healthcare provider account. The sub-process continues by comparing the patient data for each appointment request within the corresponding matching timeslot with the remote server in order to generate a plurality of favorability scores, wherein each appointment request is associated to a corresponding score from the plurality of favorability scores. According to the preferred embodiment of the present invention, the plurality of favorability scores includes at least one score selected from a group consisting of, a standard score and at least one weighted score, wherein the weighted score is assigned to at least one selection criteria. In other words, the favorability score can be a standard score based on the time and date of the creation of the appointment request from the patient accounts. Alternately, the favorability score can be a weighted score which is generated by the chosen algorithms by the provider account, which then ranks the patient accounts based on different criteria such as healthcare costs per year, estimated future health care costs per year, type of patient insurance, diagnosis, symptoms, or any combination of the previously mentioned parameters. The patient accounts are not aware of the weighting algorithms chosen by the health care provider accounts, or the ranking that the patient account has received. The sub-process ends by designating the patient account associated to a highest-scored appointment request as the optimal account.

An example on the possible criteria using the weighted algorithms is shown in FIG. 6. A weighted score option uses artificial intelligence in the scoring system. This may be useful for full risk health plans trying to contain costs by identifying high risk patients and giving them priority. As seen in FIG. 6 sample parameters or selection criteria for a 2-person weighted queue is provided. In this example, the weighted scores (favorability scores) are based on acuity of diseases and other factors as deemed appropriate. The highest total composite score gets first priority in the queue. Furthermore, according to the preferred method of the present invention, a higher corresponding score can be assigned to a patient account based on prior patient healthcare cost per year, estimated future health care cost per year, type of patient insurance etc. For example, if a patient account has been designated a higher scored health plan or is a member of a higher cost pool, then the corresponding score for that patient account would be at a higher priority compared to a low-cost utilizing patient account. In another example, if two patient accounts were in the same category, an insurance company might want to use a weighted score system to reduce the costs by treating higher risk patients first over healthier patients before the conditions of the higher risk patient requires the patient to be admitted into a more costly emergency room. In a different scenario, a combination practice comprising part concierge and part standard patients may benefit from offering priority to the concierge patients as a service. Furthermore, the favorability score can be prioritized by diagnosis or symptoms the patient is experiencing. For example, a patient with abdominal pain may be prioritized over a heart burn patient in a queue depending on the physician practice criteria. If a queue is offering a priority to two patient accounts with similar categories, and weighted composite scores, then the deciding factor would be based on the time of creating for the wish list corresponding to each patient account. Infinite number of algorithms can be used for weighting the queues. An infinite number of weighted queues can be used by the healthcare provider or an unweighted queue only.

Continuing with the example provided in FIG. 6, the algorithm chosen by the healthcare provider is as follows.

Total appointment request score=sum of weighted scores=sum of (corresponding score×weighting factor for each criterion).

Thus, according to the table in FIG. 6, the total appointment request score may be calculated as follows, using the above-mentioned algorithm.
Patient A: 1×0.0 (date of appointment request creation)+1×0.5 (symptom)+2×1 (medical history risk score)+3×1.25 (insurance plan)=6.25
Patient B: 2×0.0 (date of appointment request creation)+2×0.5 (symptom)+3×1 (medical history risk score)+2.5×1.25 (insurance plan)=6.5
Thus, patient A from FIG. 6 is the optimal account, due to a higher scored appointment request than patient B.

Alternately, if a non-weighted or standard score is used to determine the order, then the favorability score is ranked within a score based on the appointment request time and date.

As can be seen in FIG. 2, the overall method of the present invention continues by transmitting an appointment availability notification to the optimal account with the remote server (Step G). In other words, the cloud-based remote server relays the information of the appointment availability to the patient account, in the form of a text and/or email or by any other preferred method of communication chosen by the patient account of the optimal account.

Figure 7:
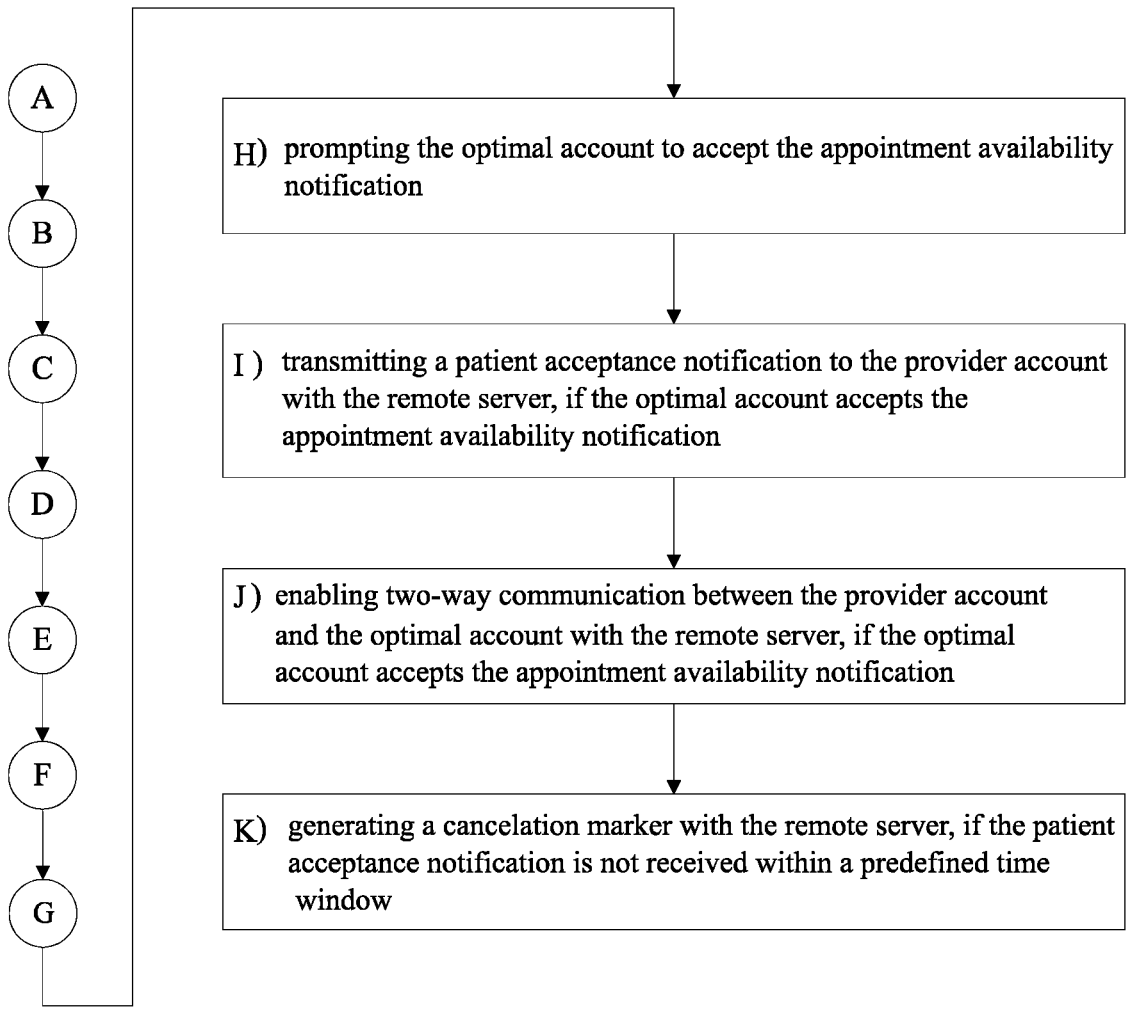
FIG. 7 is a flowchart describing an extended process of the overall method, for accepting or rejecting appointments.

As can be seen in FIG. 7, a dependent extending process for accepting or rejecting appointments according to the method of the present invention, is illustrated below. The process begins by prompting the optimal account to accept the appointment availability notification (Step H). Subsequently, if the optimal account accepts the appointment availability notification, a patient acceptance notification is transmitted to the provider account with the remote server (Step I). Further, a two-way communication is enabled between the provider account and the optimal account with the remote server, if the optimal account accepts the appointment availability notification (Step J). The mode of communication is customizable for both the healthcare provider accounts and the patient accounts. According to the preferred embodiment of the method of the present invention, each health care provider account sets a predefined time window in which the patient account can respond with an approval or a rejection of the newly available time slot. Accordingly, the method of the present invention includes, prompting the provider to edit the predefined time window with the provider PC device. For example, 30 minutes per offer may be provided typically before offering the spot to the next person in the queue. However, any other duration may be set by the provider account, as long as the intentions of the method of the present invention are not altered. The patient account then can accept or decline the appointment. If the optimal account fails to respond within the time frame selected by the health care provider account, then that information is relayed to the cloud-based server(s). Subsequently, the method proceeds to generating a cancelation marker with the remote server if the patient acceptance notification is not received within a predefined time window (Step K). The cancelation marker is a representative tag associated to the optimal account that includes a cancelation date and time. Further, the preferred method of the present invention has the ability of transmitting the appointment availability notification to a new optimal account with the remote server, if the patient acceptance notification is not received within the predefined time window.

According to the preferred embodiment of the method of the present invention, a sub-process enables the healthcare provider to find new patients when one patient cancels. The patient cancelling an appointment may be a patient account associated to an optimal account, or a random cancellation. The cancellation represents an open slot or a new addition to the plurality of appointment time slots in the healthcare provider account. The sub-process begins by providing at least one cancelation marker stored on the remote server. The cancelation marker is a representative tag associated to the optimal account and includes a cancelation date and time. The sub-process continues by removing the appointment request associated to the optimal account from the corresponding matching timeslot with the remote server if the cancelation date and time matches the desired date and time. In other words, the patient account who declined or did not respond within the medical provider or medical practice adjustable but specified time period to the appointment availability notification, is removed from the matching time slot associated with the canceled date and time. Subsequently, the sub-process continues by entering the corresponding matching timeslot into the dynamic selection process with the remote server in order to identify a new optimal account, wherein the new optimal account is from the plurality of patient accounts. Finally, an appointment availability notification is transmitted to the new optimal account with the remote server. Thus, if the patient account declines or does not respond within the predefined time frame, then the available appointment or time slot is offered to the next person in the queue having the next highest scored appointment request. Further, according to the preferred method, the patient account who declined the appointment or did not respond has to wait until a next appointment availability notification is obtained. In other words, the dynamic selection process is repeated until the patient account eventually is matched with a desired time slot from the appointment request, based on the posted availability (plurality of time slots) from the health care provider account.

Alternately, the health care provider accounts may choose to immediately share an open time slot with the corresponding patient account PC (communicate directly with the patient) or may choose to generate a custom wait time for the availability to be generated by the remote server.

The preferred method of the present invention is further capable of generating a graphical representation of the plurality of appointment timeslots for the provider account with the remote server. Additionally, the method enables automatically updating the graphical representation with the remote server, if the patient confirmation notification is received and if the cancelation marker is generated. This feature of the method of the present invention allows for automatically updating patients and providers of changes in the queue. Furthermore, the graphical representation ability enables practices/doctors to see the waitlist summary of accepted or rejected appointment slots over a decided time frame such as weekly, monthly, annually etc. Thus, the method further helps the providers and doctors to effectively monitor and keep track of their active patient list, which may also be utilized as an advertising platform.

An overall analysis of the steps of the method of the present invention, that are implemented from a patient side, and a provider side may be illustrated as follows. The patient side workflow for the method of the present invention includes the following steps, that are implemented with at least one remote server and the corresponding PC device from the patient account. The overall process begins with the patient account creating an appointment request with preferred time slots. Once the appointment request has been created, the patient account awaits a preliminary match, or if an appointment slot is immediately available the patient account will be presented with a preliminary match (matching time slot). Once the patient account matches the appointment slot, the patient account will receive a text, email or preferred method of communication chosen by the patient account with a notification for a posted availability via the remote server (appointment availability notification). The patient account then can accept or decline appointment availability notification. If the patient account accepts the appointment availability notification, then the patient account receives a confirmation via text message, email or other method of communication chosen by the patient account. If the patient account declines or does not respond within the predefined time frame, then the appointment is offered to the next person in the queue. The patient account who declined the appointment or did not respond within the predefined time frame is set back to awaiting a preliminary match from the queue based on other time slots from the appointment request. This process is repeated until the patient account eventually is matched with a desired time slot from the appointment request created by the patient account based on the posted availability from the health care provider account.

The health care provider side workflow for the method of the present invention includes the following steps, that are implemented with the at least one remote server(s) and the corresponding PC device from the health care provider account. The overall process begins with the health care provider account receiving a cancellation. Subsequently, the health care provider account may manually search for an available patient account and then manually post an appointment availability. Alternately, an automatic posting of an availability can be posted via an HL7 API interface option where a schedule is read directly from a two-way interface via the cloud-based remote server(s). Subsequently, a queue is generated by the remote server for one or more patient accounts who want the posted available slot. The resulting queue can be a standard queue based on the time and date of the creation of the wish lists from the patient accounts, or it can be a weighted queue which is generated by the chosen algorithms by the provider account, which then ranks the patient accounts based on different criteria to create a customized queue (highest appointment request scores). Once the customized queue has been created the remote server will send the corresponding patient account a text message, email or method of communication chosen by the patient account. In case of the patient account accepting the newly available time slot, the patient account will receive a text message, email or method of communication chosen by the patient account, with a confirmation for their new appointment. In case of the patient account rejecting the newly available time slot or failing to respond within the selected time frame by the health care provider account, then the remote server will send a text message, email or method of communication chosen by the patient account, to the next patient account in the queue. The initial patient account may still accept an open spot that has been presented to the next patient account in the queue because the software platform accepts confirmation from the first patient account that responds. Once a patient account has accepted the newly available time slot, the health care provider account may choose to manually enter the new appointment into an office scheduling platform, or use the automatic scheduling HL7 API interface option where the schedule is read directly from a two-way interface with the cloud-based remote server(s).

Although the invention has been explained in relation to its preferred embodiment, it is to be understood that many other possible modifications and variations can be made without departing from the spirit and scope of the invention.

What is claimed is:

1. A method for customizing priority waitlist notification for appointments, the method comprising the steps of:
   (A) providing at least one healthcare provider account managed by at least one remote server, wherein the healthcare provider account is associated with a corresponding provider personal computing (PC) device, and wherein the healthcare provider account includes a plurality of appointment timeslots;
   (B) providing a plurality of patient accounts managed by the remote server, wherein each patient account is associated with a corresponding patient PC device;
   (C) prompting each patient account to enter at least one appointment request with the patient PC device, wherein the appointment request includes at least one desired date and time, wherein the at least one date and time is included in a specific repeating seven day window;
   (D) comparing the desired date and time of the appointment request for each patient account to a predefined date and time for each of the plurality of appointment timeslots with the remote server in order to identify at least one matching timeslot, wherein the matching timeslot is from the plurality of appointment timeslots;
   (E) appending the appointment request for each patient account to a corresponding matching timeslot with the remote server;
   (F) entering the corresponding matching timeslot into a dynamic selection process with the remote server in order to identify an optimal account, wherein the optimal account is from the plurality of patient accounts;
   (G) transmitting an appointment availability notification to the optimal account with the remote server;
   (H) prompting the optimal account to accept the appointment availability notification;
   (I) transmitting a patient acceptance notification to the provider account with the remote server, if the optimal account accepts the appointment availability notification;

(J) enabling two-way communication between the provider account and the optimal account with the remote server, if the optimal account accepts the appointment availability notification;
(K) generating a cancelation marker with the remote server, if the patient acceptance notification is not received within a predefined time window;
providing at least one stored appointment request which is included in the patient account;
prompting the patient account to select the stored appointment request with the patient PC device;
prompting the patient account to edit the stored appointment request with the patient PC device;
prompting the patient account to select a specific time frame with the patient PC device, wherein the stored appointment request is periodically transmitted to the provider account until an end date of the specified time frame or until the appointment availability notification is received;
transmitting the appointment availability notification to a new optimal account with the remote server, if the patient acceptance notification is not received within the predefined time window; and
prompting the provider to edit the predefined time window with the provider PC device.

2. The method of claim 1, wherein the method comprises the steps of:
prompting the patient account to enter at least two patient datum into the appointment request with the patient PC device, wherein the at least one patient datum is at least one specific repeating seven-day window, and a second patient datum is selected from a group consisting of at least one desired date and time, at least one provider account, provider group, provider specialty, network status, and distance of a provider practice from a patient-selected location.

3. The method of claim 1, wherein the method comprises the steps of:
wherein the appointment request includes patient data;
prompting the provider to enter at least one selection criterion with the provider PC device, wherein the selection criteria is at least one datapoint selected from the group consisting of, insurance plan type, chief complaint for the visit, symptoms, patient diagnosis, prior health history, prior patient health costs, severity of illness, and concierge status;
comparing the patient data for each appointment request within the corresponding matching timeslot with the remote server in order to generate a plurality of favorability scores, wherein each appointment request is associated to a corresponding score from the plurality of favorability scores, and wherein each of the plurality of favorability scores includes at least one score selected from a group consisting of, a standard score and at least one weighted score, wherein the weighted score is assigned to at least one selection criteria; and
designating the patient account associated to a highest-scored appointment request as the optimal account.

* * * * *